United States Patent [19]

Yonco et al.

[11] Patent Number: 4,818,366
[45] Date of Patent: Apr. 4, 1989

[54] LONG LIFE REFERENCE ELECTRODE

[75] Inventors: Robert M. Yonco, LaGrange; Zoltan Nagy, Woodridge, both of Ill.

[73] Assignee: The United States of America as represented by the United States Department of Energy, Washington, D.C.

[21] Appl. No.: 79,615

[22] Filed: Jul. 30, 1987

[51] Int. Cl.$^4$ .................... G01N 27/28; G01N 27/30; G01N 27/40
[52] U.S. Cl. .................................... 204/408; 204/435
[58] Field of Search ................................ 204/408, 435

[56] References Cited

U.S. PATENT DOCUMENTS

| | | | |
|---|---|---|---|
| 2,595,042 | 4/1952 | Wyllie | 204/435 |
| 3,410,779 | 11/1968 | Whitehead et al. | 204/435 |
| 3,445,366 | 5/1969 | Vermeer | 204/435 |
| 3,463,717 | 8/1969 | Koopman et al. | 204/435 |
| 3,652,439 | 3/1972 | Ben-Yaakov et al. | 204/435 |
| 3,864,232 | 2/1975 | Handman et al. | 204/422 |
| 4,414,093 | 11/1983 | Redey et al. | 204/408 |
| 4,659,451 | 4/1987 | Fujita et al. | 204/435 |

OTHER PUBLICATIONS

McDonald et al., "External Reference Electrodes for Use in High Temperature Aqueous System", *J. of Electrochemical Soc.*, pp. 908–911, Jun., 1979.
McDonald, "Reference Electrodes for High Temperature Aqueous Systems–a Review & Assessment", *Corrosion*, pp. 75–84, NACE, 1978.
Nagy et al., "Palladium/Hydrogen Membrane Electrode for High Temperature/High Pressure Aqueous Solutions", *J. of the Electrochemical Soc.*, vol. 33, No. 11, Nov. 1986, Reprint, pp. 2232–2235.

Primary Examiner—T. Tung
Attorney, Agent, or Firm—Hugh W. Glenn; Robert J. Fisher; Judson R. Hightower

[57] ABSTRACT

An external, reference electrode is provided for long term use with a high temperature, high pressure system. The electrode is arranged in a vertical, electrically insulative tube with an upper portion serving as an electrolyte reservoir and a lower portion in electrolytic communication with the system to be monitored. The lower end portion includes a flow restriction such as a porous plug to limit the electrolyte release into the system. A piston equalized to the system pressure is fitted into the upper portion of the tube to impart a small incremental pressure to the electrolyte. The piston is selected of suitable size and weight to cause only a slight flow of electrolyte through the porous plug into the high pressure system. This prevents contamination of the electrolyte but is of such small flow rate that operating intervals of a month or more can be achieved.

6 Claims, 2 Drawing Sheets

LONG LIFE REFERENCE ELECTRODE

CONTRACTUAL ORIGIN OF THE INVENTION

The United States Government has rights in this invention pursuant to Contract No. W-31-109-ENG-38 between the U.S. Department of Energy and the University of Chicago, operator of the Argonne National Laboratory.

BACKGROUND OF THE INVENTION

The present invention relates to an external reference electrode for use in combination with high temperature, high pressure aqueous systems. Electrodes of this type can be combined with any stable sensing electrodes, such as those used for measuring pH, redox potential and the concentration of specific ions. It is also contemplated that this reference electrode can be used to make in-situ corrosion rate and corrosion potential measurements directly in process system equipment.

Reference electrodes have long been used for determining the characteristics of electrochemical systems. Single electrochemical reactions at electrodes are related by convention to the hydrogen electrode whose potential at all temperatures is taken at zero. Because of the difficulties involved in using the hydrogen electrode as standard in all situations, secondary reference electrodes have been compared with the hydrogen electrode and are widely used. Well known among these are the standard calomel electrodes. For industrial processes requiring in-line applications, other reference electrodes such as Ag/AgCl; Ag/Ag$_2$SO$_4$ or a noble metal such as gold in ferrous/ferric solution as a redox couple are more suitable for use.

Representative reference electrodes are described by Macdonald et al. in "External Reference Electrodes for Use in High Temperature Aqueous Systems", J. ELECTROCHEM. SOC., pp 908–911, June 1979. and by Macdonald in "Reference Electrodes for High Temperature Aqueous Systems - A Review and Assessment", CORROSION, pp. 75–84, NACE 1978. Internal reference electrodes operating at the temperature and pressure of the system can be unstable at temperatures above 150° C. for extended periods of time. Consequently, external electrodes housed in separate compartments maintained at ambient temperature and system pressure have become attractive alternatives. Unfortunately, these electrodes have relatively short lives due to the inevitable contamination of the reference electrode solution by the high pressure system solution. In addition, pressure differentials between electrode solutions and high pressure systems can be difficult and expensive to accurately control.

Therefore, in view of the above discussion, it is an object of the present invention to provide an improved reference electrode assembly.

It is a further object of the invention to provide a long life reference electrode to be used with high temperature and high pressure aqueous systems.

It is a further object of the present invention to substantially eliminate contamination of the reference electrode solution by the system constituents.

SUMMARY OF THE INVENTION

In accordance with the present invention, an electrode assembly is provided for a reference potential in respect to a high pressure, high temperature system. The electrode assembly includes an elongated, generally vertical tube for containing liquid electrolyte with flow restriction means at its lower portion for restricting the release of electrolyte into the high pressure, high temperature system. At the upper portion of the electrode tube is a piston that is slidably fitted therein for imparting a constant incremental pressure sufficient to urge electrolyte flow through the flow restriction into the system. The electrode is disposed in the mid-portion of the tube between the piston and flow restriction means at a location to be in contact with the liquid electrolyte. The electrode is thereby able to provide a reference electrical potential in respect to the system to be monitored.

In other aspects of the invention, the electrode assembly is positioned external to the high temperature, high pressure system but with the piston enclosed in a chamber communicating with system pressure, such that the piston weight imparts by gravity a small but constant incremental pressure to the reference electrode electrolyte. In other aspects, the electrode assembly in its upper portion includes a reservoir for the electrolyte in communication with the piston. The piston is enclosed within a flexible pouch containing a water immiscible, electrically insulative liquid for sealingly transmitting system pressure to the piston.

In yet further aspects of the invention, the electrolyte tube includes an enlarged upper portion as an electrolyte reservoir fitted to receive the piston. The lower portion of the tube is of substantially smaller diameter than the upper portion and is provided with a porous plug for restricting electrolyte flow into direct contact with the system liquid being monitored.

DETAILED DESCRIPTION OF THE DRAWINGS

The present invention is illustrated in the accompanying drawings wherein.

DETAILED DESCRIPTION OF THE PREFERRED EMBODIMENT

Figure 1:
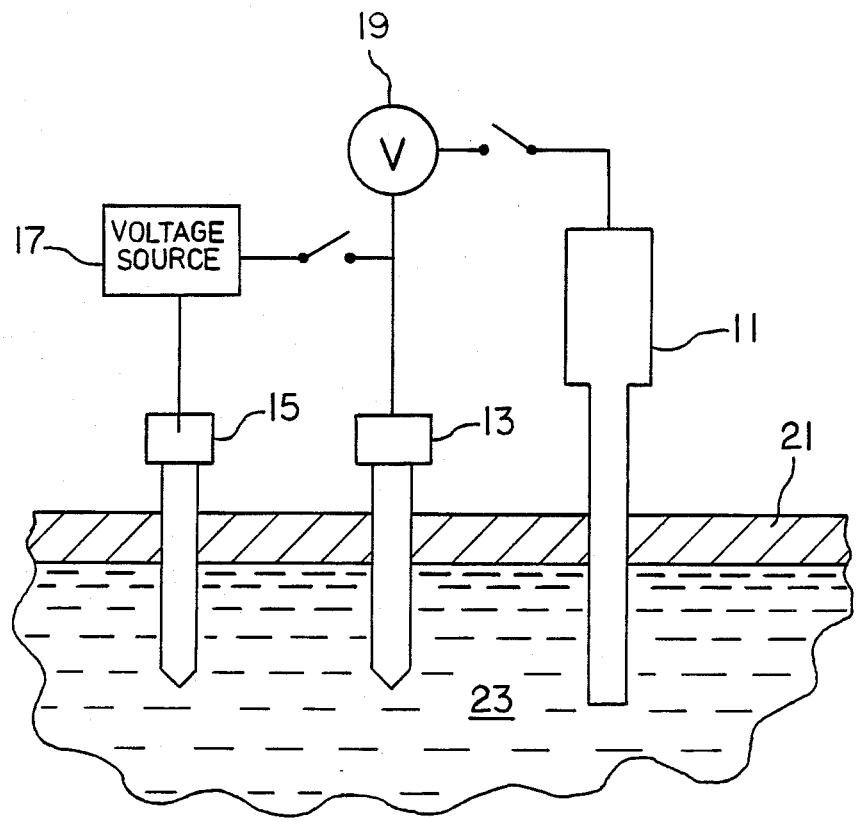
FIG. 1 is a schematic diagram illustrating an arrangement of a reference electrode in cooperation with a working electrode and a counter electrode.

FIG. 1 illustrates a simplified arrangement including a reference electrode 11, a working electrode 13, and a counter electrode 15. A voltage source 17 of alternating or direct current is shown between the working 13 and counter electrode 15. In systems where an applied voltage is not required voltage source 17 could be eliminated. A voltmeter 19 or other means for measuring electrical potential is illustrated in circuit between working electrode 13 and reference electrode 11.

As stated, FIG. 1 is a simplified arrangement and many modifications and additional components could be included. For example, the working and counter electrodes 13 and 15 advanteously can be combined in a coaxial arrangement within a single probe to eliminate inductive effects when fast pulse measurements of rapid electrode reactions are desired. The fast rising current pulse may generate an inductive EMF, even in a straight piece of wire that can be larger than the overpotential to be measured between the working and reference electrodes. Although, not shown, conventional thermocouples and pressure measuring instruments may be required depending on the use to be made of the electrode arrangement.

The reference, working and counter electrodes are illustrated, penetrating a containment wall 21 holding a process liquid system 23 that may be at elevated pressures and temperatures. Temperatures of at least 300° C. with pressures of 100 atmospheres have been demonstrated and critical to supercritical conditions are contemplated in systems to which the present invention is applicable.

The illustrated reference electrode 11 can be used with any stable sensing electrode, such as one for measuring pH, redox potential, chloride or sulfate ion concentations, etc., to provide a long life continuous monitoring sensor for the high temperature, high pressure process liquid. Working electrodes for measuring pH and redox potentials are commercially available. Electrodes for monitoring specific ions concentrations, such as chloride, sulfate, etc., have and can be assembled in accordance with the principles in the published literature. Specifically, a very stable and reliable pH sensor can be made with the combination of the reference electrode of this invention and a palladium membrane, pH sensitive electrode of low impedance. Such an electrode is described by the inventors in the Journal of Electrochemical Society, Vol. 133, No. 11, pages 2232–2235 (Nov. 1986).

Figure 2:
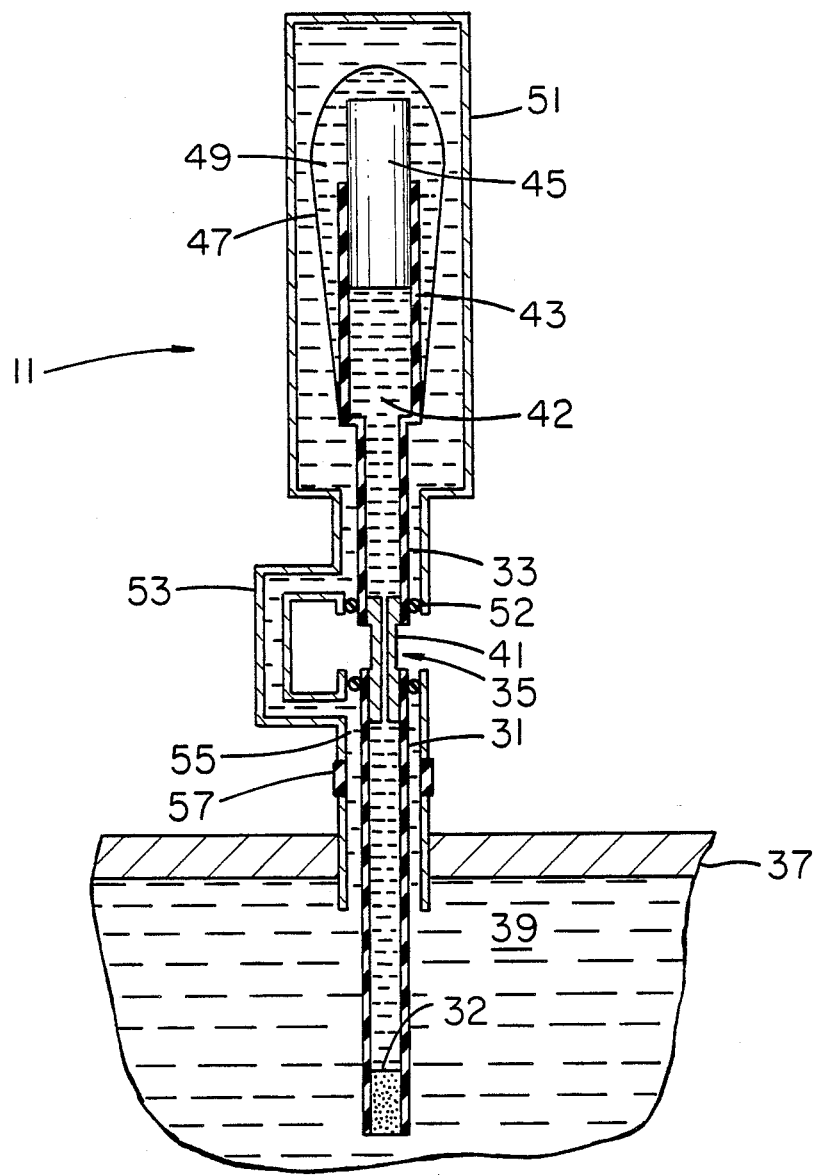
FIG. 2 is a generally schematic elevation view of a reference electrode.

Referring now to FIG. 2, a reference electrode assembly 11 is described. The electrode assembly is illustrated as a vertical tube in two portions 31 and 33 coupled to provide liquid electrolyte to a tubular metal electrode 35. The lower portion of the vertical tube 31 penetrates the containment wall 37 of the process or of a high pressure sampling cell to be monitored. The monitored process liquid 39 is in direct contact with the lower portion of vertical tube 31 and is contemplated to be at elevated temperature and pressure typically of about 300° C. and 100 atmosphere pressure. Tube 31 and 33 are of electrically insulative materials and at least in the case of tube 31, of high temperature resistant material such as polytetrafluoroethylene or alumina. Tube 31 is provided of sufficient length to place metal electrode 35 sufficiently far from the high temperature process to permit its operation at ambient temperature. Where required, cooling means (not shown) can be interposed between electrode 35 and process liquid 39. Electrical contact at position 41 permits electrical reference to electrode 35.

The upper portion of tube 33 can be of larger diameter than its lower portion to provide an electrolyte reservoir 43 with an open upper end arranged to accept a weighted piston 45. Where sufficiently large tubes are selected, reservoir 43 may be of the same diameter as tube 33. As illustrated, electrolyte reservoir 43 and piston 45 are enclosed within a flexible pouch 47 containing oil or other water immiscible, electrically insulating liquid 49 for transmitting external pressure to the piston 45. The upper portion of the electrode assembly is enclosed in a pressure chamber 51 of appropriate material to be compatable with process fluid 39.

The fluid and pressure contained by wall 37 passes to chamber 51 through a suitable by-pass 53 sealed at ring 52 around the metal electrode 35. Typically, an annular chamber 55 with an electrically insulative portion 57 encloses and seals vertical tube 31 as it penetrates containment wall 37.

Reservoir 43, tubes 31 and 33 are filled with an electrolyte 42 appropriate for use with the reference metal electrode 35. A porous plug 32 of an electrically insulative ceramic, such as alumina or zirconia, restricts the lower end of tube 31 to limit electrolyte loss into the process liquid 39.

Metal electrode 35 can be any of the known stable metal electrodes suitable for use as a reference. Typically selected are the silver/silver chloride electrode or the silver/silver sulfate electrode. Appropriate electrolytes such as alkali metal salts in aqueous solution are selected as electrolytes. For example, an internal electrolyte of potasium chloride can be selected for use with the silver/silver chloride electrode.

The electrode is of tubular shape with the appropriate electrolyte solution at the inner surface. The tubular shape permits electrolyte communication between upper tube 33 and lower tube 31. Also, alloys and other noble metal/salt electrode combinations are contemplated. In the case of a redox reference electrode, a gold metal wire in contact with ferrous/ferric solution can be used.

In the continuous, long term, unattended operation of the reference electrode, a very small continuous flow of electrolyte or other electrode solution passes from the electrolyte reservoir 43 through the tubular metal electrode 35 and porous plug 32 into the process liquid 39. The small flow is uniform as it is controlled by the weight of piston 45 which imparts a uniform and continuous pressure increment above that of the system to be monitored 39. Complicated and expensive pressure control devices are unnecessary even though the required pressure increment is minimal in comparison to the total pressure of the system. For example, a pressure differential of 0.005 atmospheres can consistantly be maintained above that of a system pressure of 100 or more atmospheres. Even with substantial fluctuations of the system pressure, this incremental, small pressure differential can be maintained by the constant exertion of piston weight.

As an example of operation of the system, a 5 ml. hypodermic syringe was used with the plunger functioning as the piston 45. The lower portion of the syringe of about 2 cm diameter, served as the electrolyte reservoir 43 and a stainless steel pipe of about 4 cm in diameter served as chamber 51. A flexible pouch of latex material was filled with silicone oil to transmit the system pressure to the outside of the weighted piston without interfering with piston movement. By providing different weights between 7.5 to 45 grams to the piston, flow rates of 11 to 68 microliters per hour of electrolyte in linear relation to the applied pressure were observed. In another combination of piston weight and porous plug, a flow rate of 0.3 microliters per hour was observed. Therefore, a reference electrode assembly of this type can contain sufficient electrolyte reserve to operate continuously for over a month without recharging.

It therefore is seen that the present invention provides a long life reference electrode for use in a process with a high temperature, high pressure system. In corrosion rate measurements, working and counter electrodes can be inserted into the process equipment to be monitored together with the reference electrode. The reference electrode also perits in-line monitoring of pH over long periods as well as particular ion concentrations and oxidation-reduction potentials within a process fluid. The reference electrode need not be maintained at the high temperature of the system, and includes an uncomplicated pressure equalization arrangement to permit close and precise pressure control of the electrode fluid over that of a process with pressure several orders of magnitude higher.

Although the present invention has been decribed in terms of a specific embodiment, various modifications or alterations may be made by one skilled in the art in the materials, process components and arrangements within the scope of the invention defined in the attached claims.

The embodiments of this invention in which an exclusive property or privilege is claimed are defined as follows:

1. An electrode assembly for providing a reference potential in respect to a high pressure, high temperature system comprising:
    an elongated, generally vertical tube for containing liquid electrolyte, said tube having an upper portion and a mid-portion disposed outside of said system and a lower portion sealingly penetrating into electrolytic communication with said high pressure, high temperature system;
    flow restriction means in the lower portion of said tube for restricting the release of electrolyte into said high pressure, high temperature system;
    pressure imparting means for applying a constant incremental pressure above the system pressure to urge a constant flow of liquid electrolyte through the flow restriction means into said system, said pressure imparting means being a piston of sufficient weight slidably fitted into the upper portion of said vertical tube to provide by gravity said constant incremental pressure as said electrolyte flows into said system regardless of the system pressure;
    pressure equalization means between said piston and said high pressure, high temperature system for balancing said piston to said system pressure, said pressure equalization means being coupled to said piston through a flexible pouch containing a water immiscible, electrically insulating liquid encompassing the upper portion of said vertical tube; and
    an electrode disposed in contact with said electrolyte in the mid-portion of said tube outside said high pressure, high temperature system for providing a reference electrical potential in respect to said system.

2. The electrode assembly of claim 1 wherein the upper portion of said tube containing said piston is enclosed in a chamber in communication with said pressure equalization means for maintaining said chamber around said piston at the pressure of said system.

3. The electrode assembly of claim 1 where the upper portion of said tube is of larger diameter than the lower portion thereof for containing a reserve of liquid electrolyte and for sealingly receiving a piston of corresponding diameter.

4. The electrode assembly of claim 1 wherein said electrode is a silver-silver chloride electrode in contact with aqueous alkali metal halide electrolyte.

5. The electrode assembly of claim 1 wherein said flow restriction means includes a porous plug at the lower end portion of said tube, and wherein the lower end portion of said tube is of substantially smaller diameter than the upper end portion containing said piston.

6. The electrode assembly of claim 1 wherein said tube is of electrically insulative material and contains a porous plug, said assembly is installed in said high temperature, high pressure system such that the porous plug is in direct contact with the system liquid to be monitored.

* * * * *